United States Patent
Williams

(10) Patent No.: US 7,802,681 B2
(45) Date of Patent: Sep. 28, 2010

(54) PACKAGING AND ASSEMBLY FOR PIPETTE

(75) Inventor: Meleri Williams, Maidstone (GB)

(73) Assignee: Smiths Group PLC, London (GB)

(*) Notice: Subject to any disclaimer, the term of this patent is extended or adjusted under 35 U.S.C. 154(b) by 1117 days.

(21) Appl. No.: 10/585,410

(22) PCT Filed: May 9, 2005

(86) PCT No.: PCT/GB2005/001757

§ 371 (c)(1),
(2), (4) Date: Jul. 7, 2006

(87) PCT Pub. No.: WO2005/110603

PCT Pub. Date: Nov. 24, 2005

(65) Prior Publication Data

US 2009/0184018 A1 Jul. 23, 2009

(30) Foreign Application Priority Data

May 15, 2004 (GB) ................... 0410923.7

(51) Int. Cl.
*B65D 83/00* (2006.01)
*A61B 17/06* (2006.01)
*B01L 3/02* (2006.01)
*C12M 3/00* (2006.01)

(52) U.S. Cl. .............. 206/363; 206/438; 73/864.24; 435/307.1

(58) Field of Classification Search ......... 206/363–367, 206/438, 758, 303, 305, 306, 38, 37, 39.4, 206/380; 73/864.01, 864.24; 435/307.1

See application file for complete search history.

(56) References Cited

U.S. PATENT DOCUMENTS

| | | | | |
|---|---|---|---|---|
| 2,667,394 A * | 1/1954 | Goetz et al. | ................ | 206/380 |
| 3,307,711 A * | 3/1967 | Berry | ................ | 211/132.1 |
| 3,525,264 A | 8/1970 | Nieglos et al. | | |
| 3,648,891 A * | 3/1972 | Katz et al. | ................ | 206/380 |
| 3,991,627 A | 11/1976 | Laird et al. | | |
| 4,116,333 A * | 9/1978 | Pavel | ................ | 206/380 |
| 5,417,926 A * | 5/1995 | Bouveret | ................ | 206/364 |
| 5,431,280 A * | 7/1995 | Bryant | ................ | 206/363 |
| 6,199,695 B1 * | 3/2001 | Takeo | ................ | 206/380 |
| 6,439,276 B1 * | 8/2002 | Wood et al. | ................ | 206/365 |
| 7,390,648 B1 | 6/2008 | Palacios-Boyce | | |
| 2006/0032773 A1 * | 2/2006 | Booker et al. | ................ | 206/364 |
| 2007/0125675 A1 * | 6/2007 | Booker et al. | ................ | 206/438 |

FOREIGN PATENT DOCUMENTS

WO    00/65137    11/2000
WO    2004/028227   4/2004

* cited by examiner

*Primary Examiner*—J. Gregory Pickett
(74) *Attorney, Agent, or Firm*—Louis Woo

(57) ABSTRACT

Packaging for an ICSI pipette (50) has a base (10) and a slider (20) on which the pipette is retained by clips (29) and (36). The base (10) has a transparent rod (16) projecting above the thin end (52) of the pipette (50), acting as a lens to enable the tip of the pipette to be viewed. A grip portion (26) on the slider (20) projects above the pipette (50) and the rod (16) to enable the slider to be moved relative to the base such that the thick end (52) of the pipette projects beyond the end of the base for access and removal.

9 Claims, 3 Drawing Sheets

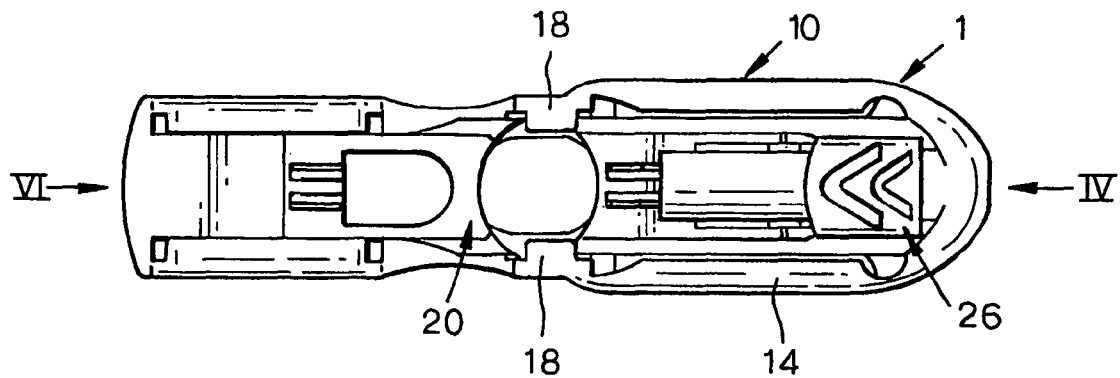
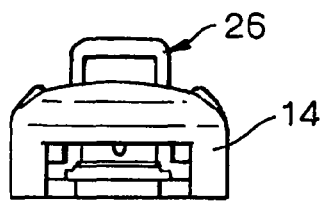
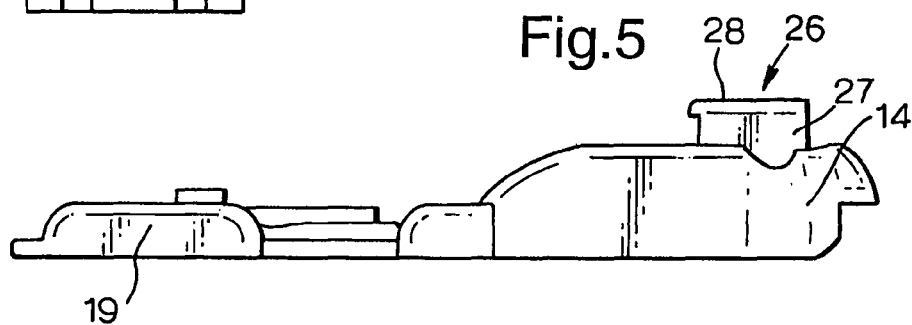
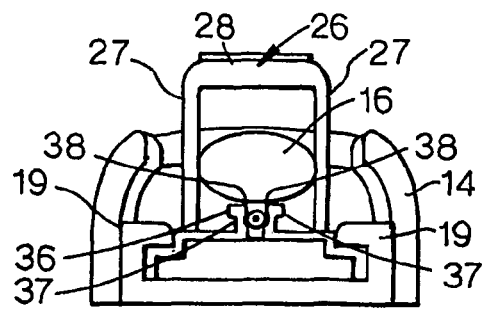

PACKAGING AND ASSEMBLY FOR PIPETTE

This invention relates to packaging of the kind for an ICSI pipette.

The ICSI (intracytoplasmic sperm injection) procedure involves injecting a single sperm into an egg using a fine pipette. ICSI pipettes take the form of a glass tube one end of which is tapered to a very fine tip suitable for injecting into the egg. These pipettes are very delicate and are easily broken during transport and handling. The pipettes are packed before use in a protective container but it can be difficult to extract the pipette without damage. Also, it may be necessary to handle the pipettes excessively in order to remove them from the packaging, which is undesirable.

There are also other devices that are difficult to transport and handle because of their delicate nature.

It is an object of the present invention to provide an alternative form of packaging and an assembly of a pipette and packaging.

According to one aspect of the present invention there is provided packaging of the above-specified kind, characterised in that the packaging includes a base member, a slider slidable relative to the base member, and that the slider is configured to receive and support the pipette and is movable between a first position where both ends of the pipette are contained within the length of the packaging and a second position where one end of the pipette projects beyond one end of the base member.

The slider may include a raised grip portion by which the slider can be displaced relative to the base member. The base member may include a portion arranged to extend over a part at least of the pipette. The grip portion is preferably arranged to extend above the portion on the base member, which may include a lens arranged to magnify a part of the pipette. Preferably the portion on the base member includes a transparent rod with a convex surface, the rod being arranged to extend axially above the pipette. The rod may be mounted at an end of the base member opposite the one end and may project towards the one end. The slider preferably includes a clip arranged to receive the pipette.

According to another aspect of the present invention there is provided an assembly of an ICSI pipette having a thick end and a thin end and packaging according to the above one aspect of the invention.

The one end of the pipette is preferably the thick end.

An assembly of an ICSI pipette in packaging, according to the present invention, will now be described, by way of example, with reference to the accompanying drawings, in which:

FIG. 3 is a plan view of the assembly without the pipette;

FIG. 4 is an end view of the rear of the assembly without the pipette along the arrow IV of FIG. 3;

FIG. 5 is a side elevation view of the assembly without the pipette;

FIG. 6 is an end view of the forward end of the assembly along the line VI of FIG. 3;

Figure 1:
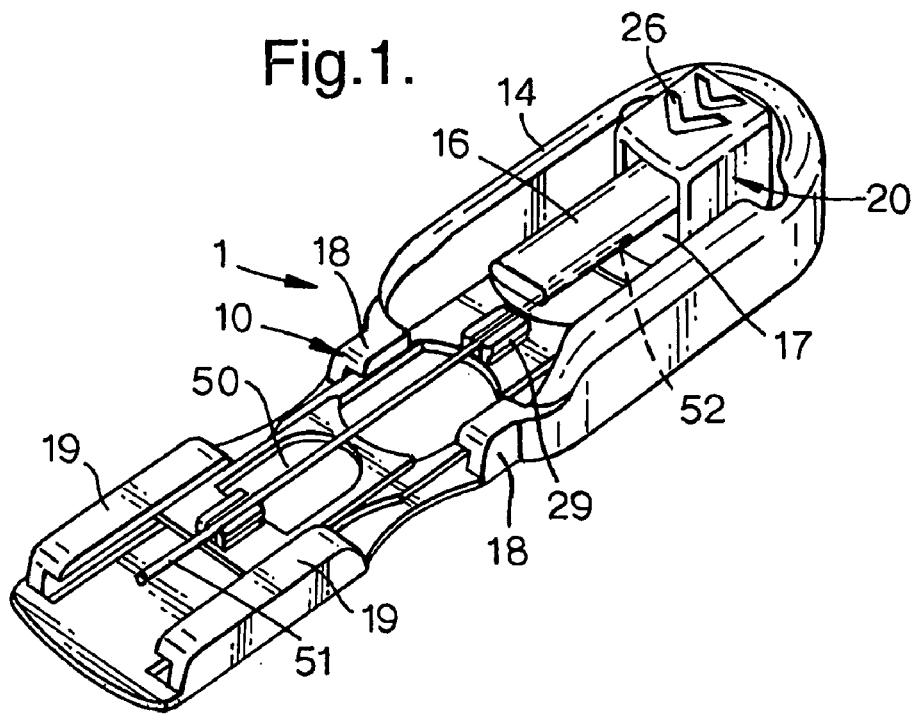
FIG. 1 is a perspective view of the assembly with the packaging in its stored position.
Figure 2:
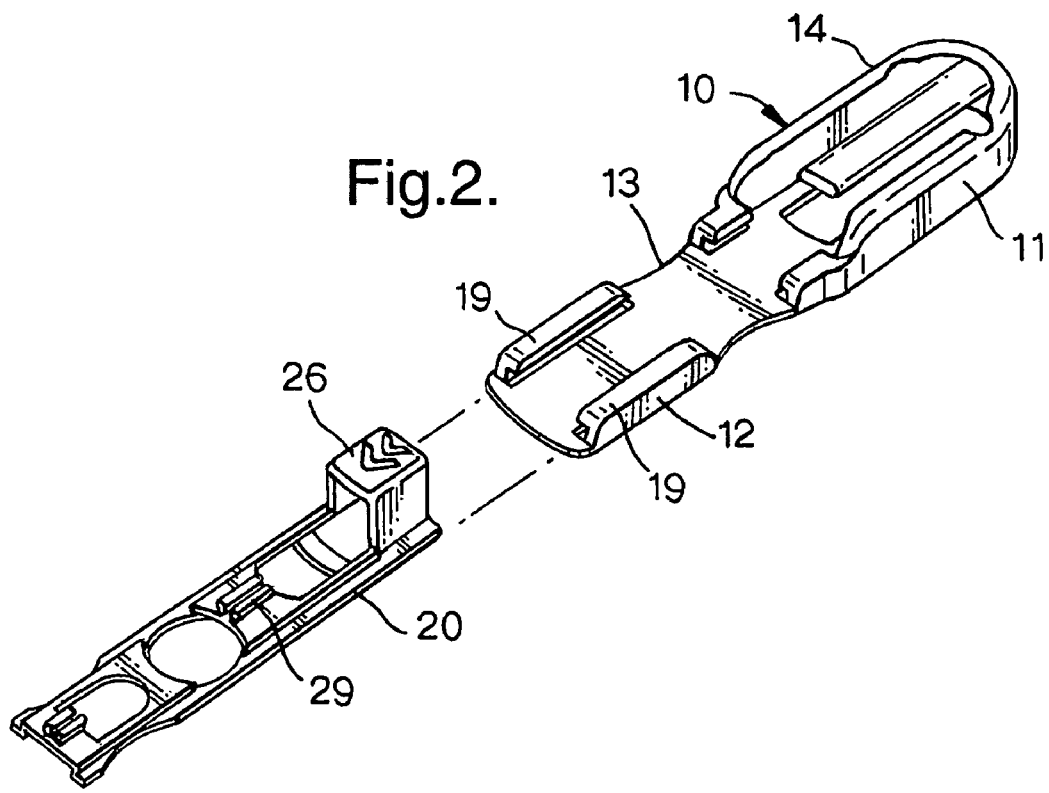
FIG. 2 is a perspective view of the two components of the packaging separated from one another.
Figure 7:
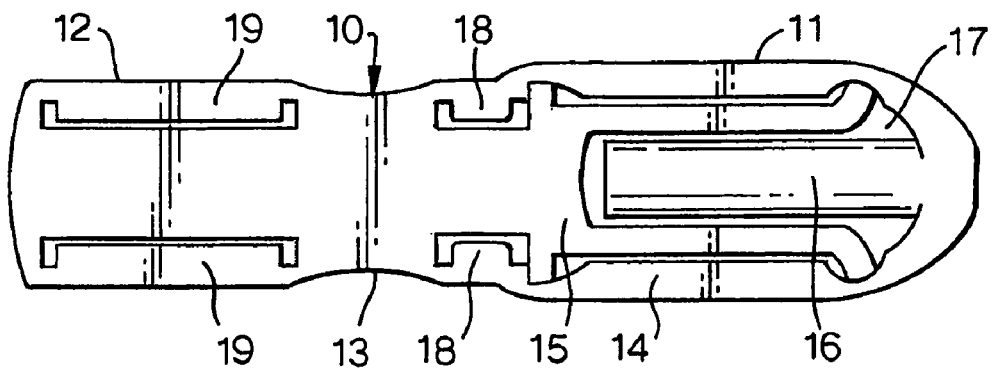
FIG. 7 is a plan view of the base.
Figure 8:
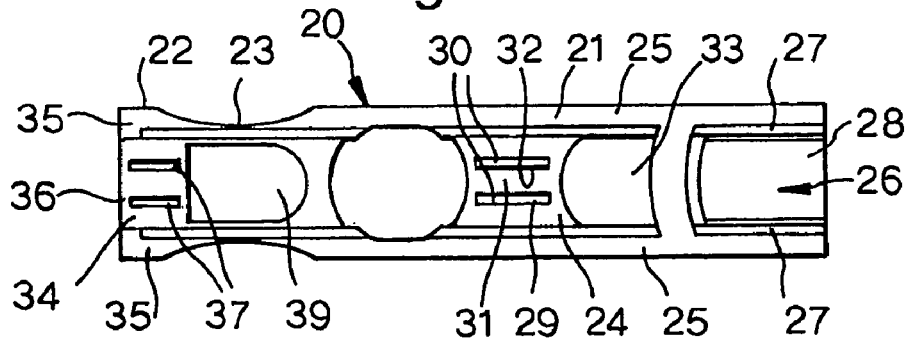
FIG. 8 is a plan view of the slider.

The packaging 1 consists of two components namely a base 10 and a slider 20, and forms an assembly with a conventional glass ICSI pipette 50 mounted on the slider. The assembly would normally also include an outer protective envelope (not shown) to maintain sterility and which is removed before use.

The base 10 is a single-piece, integral moulding of a hard, optically-transparent plastics material, such as MABS and has a generally elongate rectangular shape comprising a rear portion 11 and a forward portion 12 separated from one another by a waist region 13. The rear portion 11 has a curved peripheral wall 14 extending along both sides and the rear end of a base plate 15. The wall 14 is also curved in section to provide a concave inner surface and a convex outer surface. The rear part of the wall 14 supports a rod 16 projecting forwardly axially midway along the base 10 and raised above an opening 17 in the base plate 15. The rod 16 is bi-convex in section to form an elongate magnifying lens and terminates just short of the forward end of the wall 14. Two short L-shape channel members 18 project upwardly from the base plate 15 at opposite sides, between the forward end of the wall 14 and the waist region 13. The forward portion 12 has two longer channel members 19 extending along opposite sides and aligned with the rear channel members 18.

The slider 20 is also a single piece integral moulding of a plastics material, such as stabilised polypropylene, and is coloured for identification purposes. The slider 20 comprises a rear portion 21 and a forward portion 22 separated from one another by a waist region 23. The rear portion 21 comprises a flat plate 24 having two rails 25 extending along opposite sides, which are shaped to slide within the rear channel members 18. At its rear end, the rear portion 21 has an upwardly-extending thumb grip bridge 26 of inverted U shape. The two uprights 27 of the grip 26 extend up between the wall 14 and the lens 16, with its top platform 28 extending horizontally over the lens. A support and retaining member or clip 29 projects from the upper surface of the slider 20 midway across its width and just rearwardly of the waist region 23. The clip 29 takes the form of two ribs 30 extending parallel to the slider 20 and closely spaced from one another to form a recess 31 in which the pipette 50 is received. The upper end of each rib 30 is formed with a shallow lip 32 projecting towards one another so that the recess 31 is slightly narrower at its upper end. A window 33 opens through the slider 20 between the ribs 30 and the grip 26. Similarly, the forward portion 22 has a flat plate 34 with two side rails 35, which slide within the channel members 19 at the forward end of the base 10. The forward portion 22 also has a clip 36 provided by a pair of ribs 37 with inturned lips 38 (FIG. 6) aligned with the clip 29. A window 39 opens through the slider 20 to the rear of the clip 36.

The pipette 50 is in the form of a glass tube about 57 mm long with an external diameter at its rear end 51 of about 1 mm and an external diameter at its forward end 52 of about 7 micron. The rear end 51 of the pipette 50 is clipped into the clip 36 at the forward end of the slider 20, the other clip 29 receiving the pipette towards its forward end but before it reduces in diameter. The forward end 52 of the pipette 50 extends beneath the lens 16 and terminates a short distance away from with the forward edge of the grip bridge 26 so that this does not obscure viewing of the tip of the pipette. In this way, the delicate forward end 52 of the pipette 50 is protected by the lens 16 from contact when the slider 20 is in its stowed, first position and the lens enables the tip of the pipette to be viewed in a magnified form so that the user can confirm that it is undamaged. In this stowed position, both the rear end 51 and the forward end 52 of the pipette 50 are contained within the length of the packaging.

Figure 9:
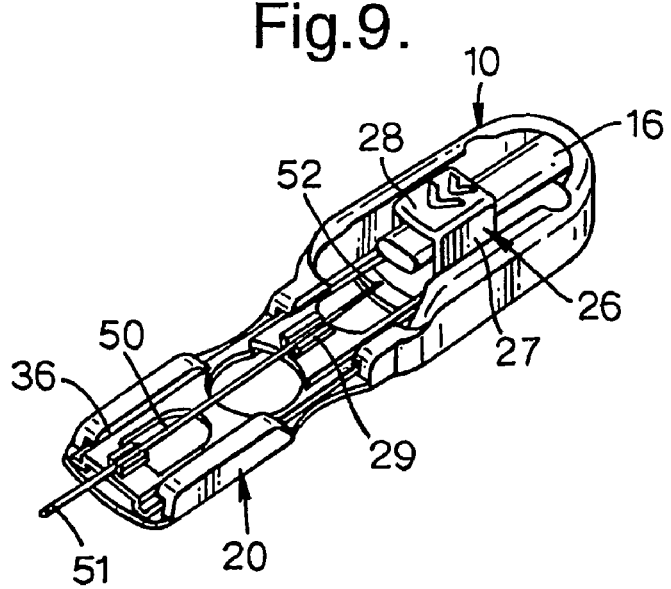
FIG. 9 is a perspective view of the assembly with the slider in its forward position.

When the user wishes to remove the pipette 50 from its packaging, he grips the grip bridge 26 with his thumb and pushes it forwardly so that the slider 20 moves forwardly relatively to the base 10 with the rails 25 and 35 sliding in the channel members 18 and 19. When the slider 20 has been fully displaced to its second, forward position, as shown in FIG. 9, the forward end 22 of the slider 20 lies level with the forward end of the base 10. In this position, the forward end 52 of the pipette 50 is located forwardly of the end of the lens 16 and the rear end 51 of the pipette projects beyond the forward end of the base 10. The user can now grip the pipette 50 by its rear end 51 and angle it upwardly slightly to pull it out of the clips 29 and 36 so that it can be connected to a suitable device for supplying the sperm to the pipette.

The packaging provides a high degree of protection to the pipette while the sliding arrangement enables the pipette to be removed easily from the packaging with a low risk of damage. The lens is useful in enabling the pipette to be checked before removal so that an alternative pipette can be provided if need be. The colour of the slider can be selected to enable coding of different types of pipette or to enable pipette packaging to be coded for particular patients.

The invention claimed is:

1. Packaging for ICSI pipette, characterized in that the packaging includes a base member, a slider slidable relative to the base member, and that the slider is configured to receive and support the pipette and is movable between a first position where both ends of the pipette are contained within the length of the packaging and a second position where one end of the pipette projects and is exposed beyond one end of the base member and the packaging, wherein the base member comprises a portion that includes a lens arranged to magnify a part of the pipette.

2. Packaging according to claim 1, characterized in that the slider includes a raised grip portion by which the slider can be displaced relative to the base member.

3. Packaging according to claim 1, characterized in that the base member includes a portion arranged to extend over a part at least of the pipette.

4. Packaging according to claim 1, characterized in that the slider comprises a raised grip portion arranged to extend above a portion on the base member.

5. Packaging according to claim 1, characterized in that the portion on the base member includes a transparent rod with a convex surface, and that the rod is arranged to extend axially above the pipette.

6. Packaging according to claim 5, characterized in that the rod is mounted to an end of the base member opposite the one end and projects towards the one end.

7. Packaging according to claim 1, characterized in that the slider includes a clip arranged to receive the pipette.

8. An assembly of an ICSI pipette having a thick end and a thin end, and packaging according to claim 1.

9. An assembly to claim 8, characterized in that the one end of the pipette is the thick end.

* * * * *